(12) United States Patent
Garvey

(10) Patent No.: US 10,736,683 B2
(45) Date of Patent: Aug. 11, 2020

(54) EXPANDING SPINAL ANCHOR

(71) Applicant: GLOBUS MEDICAL, INC., Audubon, PA (US)

(72) Inventor: Brian Garvey, Media, PA (US)

(73) Assignee: Globus Medical, Inc., Audubon, PA (US)

( * ) Notice: Subject to any disclaimer, the term of this patent is extended or adjusted under 35 U.S.C. 154(b) by 186 days.

(21) Appl. No.: 16/054,169

(22) Filed: Aug. 3, 2018

(65) Prior Publication Data

US 2018/0344373 A1 Dec. 6, 2018

Related U.S. Application Data

(60) Continuation of application No. 14/854,195, filed on Sep. 15, 2015, now Pat. No. 10,064,669, which is a division of application No. 13/086,972, filed on Apr. 14, 2011, now Pat. No. 9,161,794.

(51) Int. Cl.
*A61B 17/84* (2006.01)
*A61B 17/68* (2006.01)
*A61B 17/86* (2006.01)
*A61B 17/70* (2006.01)

(52) U.S. Cl.
CPC .......... *A61B 17/844* (2013.01); *A61B 17/686* (2013.01); *A61B 17/7032* (2013.01); *A61B 17/864* (2013.01); *A61B 17/866* (2013.01); *A61B 17/8615* (2013.01); *A61B 17/8625* (2013.01); *A61B 17/8685* (2013.01); *A61B 17/7035* (2013.01); *A61B 2017/8655* (2013.01)

(58) Field of Classification Search
CPC .................. A61B 7/844; A61B 17/686; A61B 2017/0429
See application file for complete search history.

(56) References Cited

U.S. PATENT DOCUMENTS

| 5,209,753 | A | 5/1993 | Biedermann |
| 5,217,462 | A | 6/1993 | Asnis |
| 5,489,210 | A | 2/1996 | Hanosh |
| 5,601,558 | A | 2/1997 | Torrie |
| 5,713,904 | A | 2/1998 | Errico |
| 5,827,285 | A | 10/1998 | Bramlet |
| 5,968,044 | A | 10/1999 | Nicholson |
| 6,168,597 | B1 | 1/2001 | Biedermann |
| 6,290,701 | B1 | 9/2001 | Enayati |
| 6,575,976 | B2 | 6/2003 | Grafton |
| 6,579,290 | B1 | 6/2003 | Hardcastle |
| 6,613,053 | B1 | 9/2003 | Collins |

(Continued)

*Primary Examiner* — David W Bates

(57) ABSTRACT

An anchor for a pedicle screw having an anchor body comprising a proximal end, a proximal portion, a distal portion, and a distal end, and a through-hole through the anchor body from the proximal end to the distal end. The through-hole defines a long axis of the anchor, and is provided with undersized female threads in the proximal portion and a reduced inner diameter in the distal portion. The reduced inner diameter causes expansion of at least the distal portion of the anchor body when a screw is inserted into the through-hole. The anchor is further provided with a plurality of ridges on an exterior surface of the anchor body, the ridges configured to reduce the likelihood of pullout when the anchor is inserted into a vertebra and a screw is inserted into the through-hole.

18 Claims, 4 Drawing Sheets

(56) References Cited

U.S. PATENT DOCUMENTS

| | | |
|---|---|---|
| 6,648,893 B2 | 11/2003 | Dudasik |
| 6,668,688 B2 | 12/2003 | Zhao |
| 6,733,506 B1 | 5/2004 | Mcdevitt |
| 7,074,203 B1 | 7/2006 | Johanson |
| 7,481,829 B2 | 1/2009 | Baynham |
| 7,582,107 B2 * | 9/2009 | Trail ............... A61B 17/8635 606/304 |
| 7,794,483 B2 | 9/2010 | Capanni |
| 7,794,484 B2 | 9/2010 | Stone |
| 7,857,840 B2 | 12/2010 | Krebs |
| 7,867,264 B2 | 1/2011 | Mcdevitt |
| 7,879,036 B2 | 2/2011 | Biedermann |
| 7,896,907 B2 | 3/2011 | Mcdevitt |
| 8,388,660 B1 * | 3/2013 | Abdou ............ A61B 17/8685 606/267 |
| 2001/0049528 A1 | 12/2001 | Kubota |
| 2002/0147454 A1 | 10/2002 | Neto |
| 2004/0049197 A1 | 3/2004 | Barbera Alacreu |
| 2004/0172033 A1 | 9/2004 | Bonutti |
| 2004/0176767 A1 | 9/2004 | Bickley |
| 2004/0254581 A1 | 12/2004 | Leclair |
| 2005/0137596 A1 | 6/2005 | Uwaydah |
| 2005/0216012 A1 | 9/2005 | Willmen |
| 2006/0074421 A1 | 4/2006 | Bickley |
| 2006/0095040 A1 | 5/2006 | Schlienger |
| 2008/0183220 A1 * | 7/2008 | Glazer ................ A61B 17/686 606/303 |
| 2008/0208264 A1 | 8/2008 | Lazarof |
| 2009/0105771 A1 | 4/2009 | Lei |
| 2009/0171396 A1 | 7/2009 | Baynham |
| 2009/0192552 A1 * | 7/2009 | Andersen ........... A61B 17/8685 606/302 |
| 2009/0248089 A1 | 10/2009 | Jacofsky |
| 2009/0254124 A1 | 10/2009 | Bickley |
| 2009/0264937 A1 | 10/2009 | Parrott |
| 2009/0281580 A1 | 11/2009 | Emannuel |
| 2010/0016905 A1 | 1/2010 | Greenhalgh |
| 2010/0042164 A1 | 2/2010 | Lee |
| 2010/0082072 A1 | 4/2010 | Sybert |
| 2010/0100135 A1 | 4/2010 | Phan |
| 2010/0145396 A1 | 6/2010 | Thornes |
| 2010/0185244 A1 | 7/2010 | Gooch |
| 2010/0217325 A1 | 8/2010 | Hochschuler |
| 2010/0228301 A1 | 9/2010 | Greenhalgh |
| 2010/0298888 A1 | 11/2010 | Graf |
| 2011/0071579 A1 | 3/2011 | Reach, Jr. |

* cited by examiner

EXPANDING SPINAL ANCHOR

CROSS REFERENCE TO RELATED APPLICATION

This application is a continuation of U.S. patent application Ser. No. 14/854,195 filed on Sep. 15, 2015 which is a divisional of U.S. application Ser. No. 13/086,972 filed Apr. 14, 2011, which is incorporated by reference herein in its entirety for all purposes.

FIELD OF THE INVENTION

The disclosure is directed to a device for securely attaching a spinal construct to vertebrae and, in particular, to bone screws and anchors for bone screws.

BACKGROUND OF THE DISCLOSURE

Misalignment of the vertebrae in the lumbar region of the spine can result in chronic pain and other complications due to abnormal motion of the vertebrae, as well as nerve compression by the misaligned vertebrae. Misalignment can result from a number of different conditions, such as, e.g., osteoporosis, scoliosis, degeneration or herniation of a spinal disc, tumor, or vertebral fracture.

Misalignment of vertebrae can be corrected with a spinal fusion. In this procedure, two or more vertebrae are joined together, preventing any misalignment or abnormal motion. The vertebrae are fused by placing bone grafts between the vertebrae and allowing them to grow together. The fusion process may take 6-12 months. During this time, the vertebrae must be held motionless relative to one another or the fusion will be unsuccessful.

To hold the vertebrae motionless, they may be joined together by a metal rod that is attached to screws placed into each vertebra. The typical screw path is through a pedicle and into the vertebral body. The pedicle and outer portion of the vertebral body are composed of cortical bone, providing a solid support for the proximal two-thirds of the bone screw. The interior of the vertebral body, however, is composed of cancellous bone, which does not provide as strong of a support for the distal one-third of the bone screw.

Poor support in the cancellous portion of the vertebral body may contribute to toggling or migration of the bone screw. Toggling or migration may be caused by powerful in vivo forces applied to the metal rod joining the vertebrae. These biomechanical forces are the result of normal movement, but the rod must provide resistance against them for the fusion to be successful.

Additional factors, including patient age and osteoporosis, may negatively affect the interface between the screw and the bone. Expansion of the screw path through the pedicle, which may be caused by factors such as screw strippage or revision due to misalignment, may also weaken the bone-screw interface. A poor quality bone-screw interface may lead to pullout of the screw, as well as toggling or migration.

Accordingly, there is a need for bone screws that provide an enhanced bone-screw interface, especially in the cancellous region of the vertebral body. The enhanced interface reduces incidents of pullout and toggling.

SUMMARY OF THE INVENTION

The disclosure meets the foregoing need and uses expanding screws to increase the surface area in which the bone screw contacts the bone, which results in a significant increase in the strength of the construct and other advantages apparent from the discussion herein.

An anchor for a pedicle screw having an anchor body comprising a proximal end, a proximal portion, a distal portion, and a distal end, and a through-hole through the anchor body from the proximal end to the distal end. The through-hole defines a long axis of the anchor, and is provided with undersized female threads in the proximal portion and a reduced inner diameter in the distal portion. The reduced inner diameter causes expansion of at least the distal portion of the anchor body when a screw is inserted into the through-hole. The anchor is further provided with a plurality of ridges on an exterior surface of the anchor body, the ridges configured to reduce the likelihood of pullout when the anchor is inserted into a vertebra and a screw is inserted into the through-hole.

Additional features, advantages, and embodiments of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION OF THE DISCLOSURE

Figure 1:
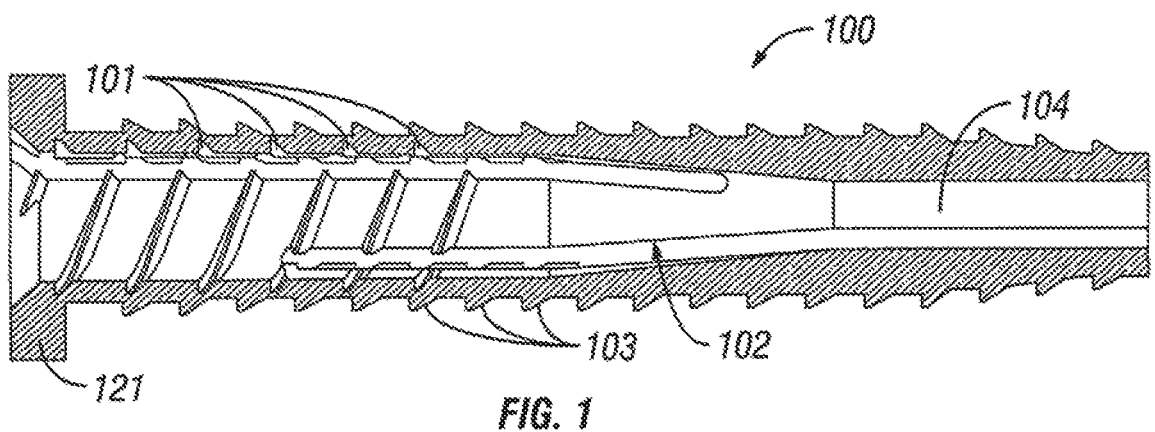
FIG. 1 shows a cutaway view of an expanding anchor for a pedicle screw, according to an aspect of the disclosure.

The embodiments of the disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure, which is defined solely by the appended claims and applicable law. Moreover, it is noted that like reference numerals represent similar parts throughout the several views of the drawings.

The interface between pedicle screws and the vertebrae is critical for posterior spinal fusion constructs. As patients age, osteoporosis and other factors decrease the potential stability of the bone-screw interface, particularly in the cancellous region of the vertebral body. In general, as the surface area in which the screw contacts the bone is increased, so is the strength of the construct.

One aspect of the disclosure provides a way to locally increase the surface contact area of the bone-screw interface in the region of greatest need, inside the cancellous vertebral body. This aspect also provides a means by which pedicle screws can be revised, due to misplacement, screw strippage, etc. without increasing the diameter of the screw path through the pedicle.

Figure 4:
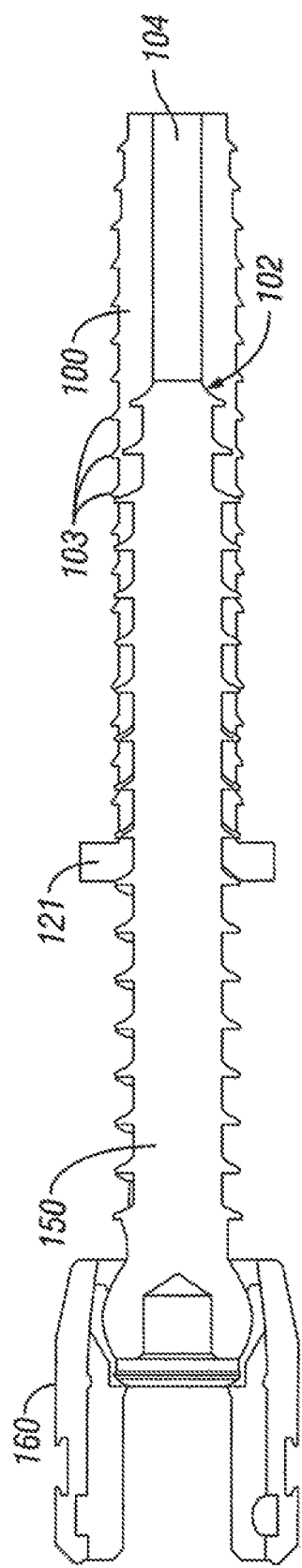
FIG. 4 shows a cutaway view of the expanding anchor in FIG. 1 with a partially inserted pedicle screw.

FIG. 1 shows a cutaway view of an expanding anchor for a pedicle screw, according to an aspect of the disclosure. The anchor 100 may be inserted into the pedicle, and a pedicle screw 150 may be inserted into a through-hole 104 in the anchor 100, as shown in FIG. 4. The through-hole 104 may define a long axis of the anchor. The anchor 100 may be constructed from any suitable material, such as, e.g., polyether ether ketone (PEEK). The anchor 100 may contain a thread form 101 to accept the pedicle screw 150, and the thread 101 may be undersized with respect to the pedicle screw 150. As the pedicle screw 150 advances, it may expand the anchor 100, as well as dig into the anchor 100. Consequently, the construct stability may be dispersed over two interfaces: the interface between the pedicle screw 150 and the anchor 100, and the interface between the anchor 100 and vertebral body (not shown).

The anchor 100 may be a cylinder machined with one or more of the following distinct features, which may serve to increase the strength of pedicle screw constructs and moreover reduce screw pullout, migration, and/or toggling. The cylinder may be constructed or formed from any suitable material, such as, e.g., polyether ether ketone (PEEK), Tandium Aluminum Vandium (TAV).

The proximal half of the anchor 100 that accepts the pedicle screw 150 may contain undersized threads 101 of the same pitch as the bone screw. The undersized threads 101 may increase the stability of the screw-anchor interface. In addition, the undersized threads 101 may provide for some degree of expansion within the pedicle path. In another embodiment, the proximal half of the anchor 100 may have mating threads that do not allow for expansion proximally or distally.

The distal half of the anchor 100, and more particularly the distal third of the anchor 100, may contain a reduced inner diameter 102. This reduced, stepped, or narrowed inner diameter 102 may create a dimensional interference between anchor 100 and pedicle screw 150 such that it forces the outer diameter of the anchor to increase by predetermined amount. The location of the reduced inner diameter 102 may cause significantly greater expansion in the distal one-third of the anchor 100, which corresponds to the cancellous region of the vertebral body.

Pullout resistance of the screw-anchor interface may be increased by the dimensional interference created by the undersized, tapped threads 101 and the reduced inner diameter 102. In addition, the pedicle screw 150 may be forced to cut slightly into the anchor 100, further increasing the frictional connection therebetween and pullout resistance.

Figure 2A:
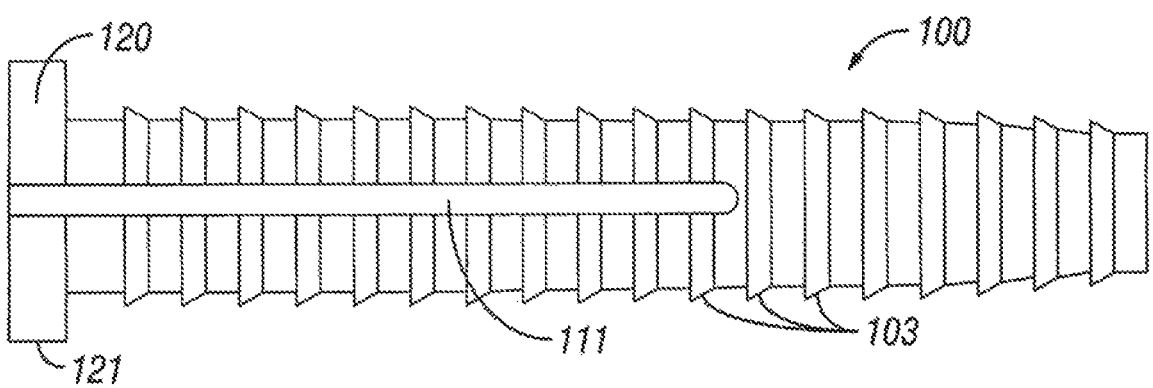
FIGS. 2A and 2B show a first side view and a second side view, respectively, of the expanding anchor in FIG. 1.
Figure 2B:
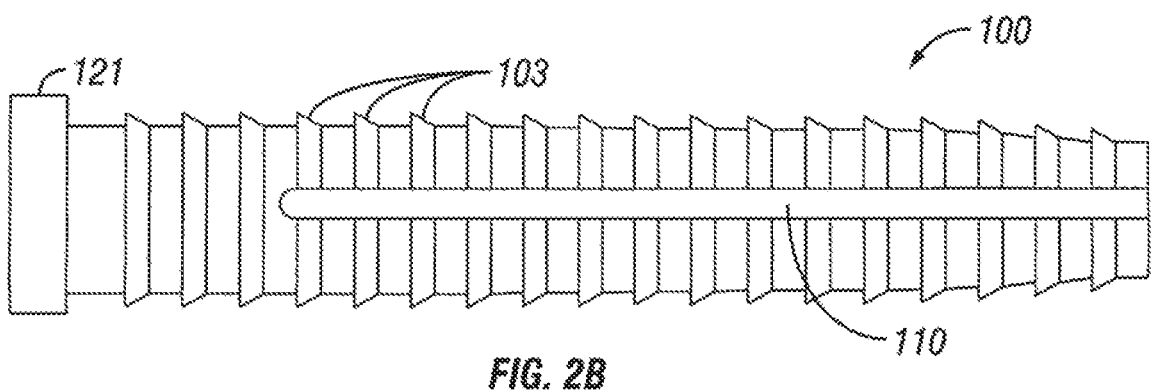

FIGS. 2A and 2B show a first side view and a second side view, respectively, of the expanding anchor in FIG. 1. Expansion of anchor 100 may be aided by four cuts 110, 111 at 90° that run parallel to the axis of the anchor 100. Two cuts 110 may run proximally from the distal end, while two cuts 111 may run distally from the proximal end. The orientation of the axial cuts 110, 111 may result in proximal expansion, as well as significantly increased expansion in the distal one-third of the anchor. Such expansion may reduce both construct pullout and construct migration or "toggling." Other expansion constructions are contemplated and are within the spirit and scope of the disclosure. For instance, slits are only provided on the distal ⅓ of the anchor so that expansion only occurs in that area.

As the pedicle screw 150 causes the outside diameter of the anchor 100 to increase, circumferential ridges 103 on the outside of the anchor may be forced into the surrounding bone. These ridges 103 are cut in a way as to provide maximum frictional force between the anchor 100 and when the anchor is subjected to a force in a direction opposite of insertion.

Figure 3:
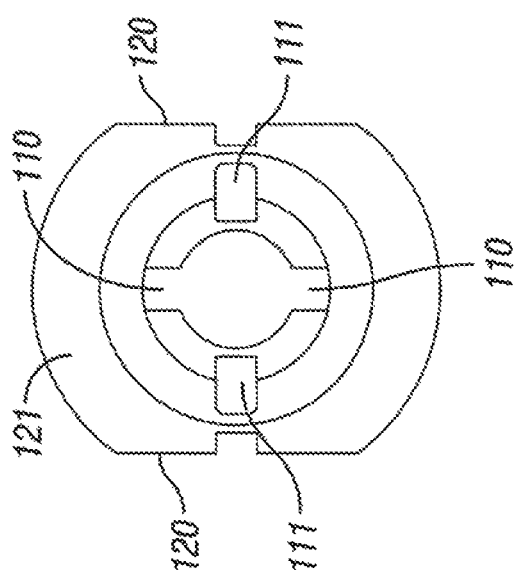
FIG. 3 shows a top view of the expanding anchor in FIG. 1.

FIG. 3 shows a top view of the expanding anchor in FIG. 1. The anchor 100 may include flats 120 on the proximal portion to engage an instrument (not shown) that prevents rotation of the anchor. Other shapes are contemplated to provide the same functionality without departing from the spirit and scope of the disclosure. The anchor 100 may alternately or additionally include a lip 121 that prevents the anchor from moving forward into the vertebra as the pedicle screw 150 is inserted.

FIG. 4 shows a cutaway view of the expanding anchor in FIG. 1 with a partially inserted pedicle screw 150. FIG. 4 also shows a driver 160, which may be used to insert pedicle screw 150 into anchor 100. Pullout resistance of the anchor-bone interface may be increased by the dimensional interference created by the undersized, tapped threads 101; the reduced inner diameter 102; and the outer ridges 103. As the inner diameter is increased, the ridges 103 may be forced into the bone, thereby reducing the possibility of back-out.

The anchor 100 and associated surgical procedure may be compatible with minimally invasive surgical techniques, rather than the open surgical techniques that have traditionally characterized spinal fusion procedures. The anchor 100 may be used as an adjunct to pedicle screws in cases of poor bone quality, as well as in cases of screw revision, regardless of the bone quality.

As noted above, the interface between pedicle screws and the vertebrae is critical for the stability of posterior spinal fusion constructs. As patients age, osteoporosis and other factors decrease the potential stability of the bone-screw interface, particularly in the cancellous region of the vertebral body. In general, as the surface area in which the screw contacts the bone is increased, so is the strength or the construct.

An additional aspect of the disclosure provides a way to locally increase the surface contact area of the bone-screw interface in the region of greatest need, inside the cancellous vertebral body. This may be achieved by mechanically increasing the diameter of the screw in the distal one-third of the screw after the screw has been inserted into the vertebral body in a collapsed position.

Screws constructed according to this aspect of the invention may increase the distal diameter of the screw via mechanical actuation. Furthermore, such screws may have a poly-axial design and include components that are compatible with other poly-axial designs and systems, such as, e.g., a tulip, a clamp, a wedge, and a bone screw with threads.

Figure 5:
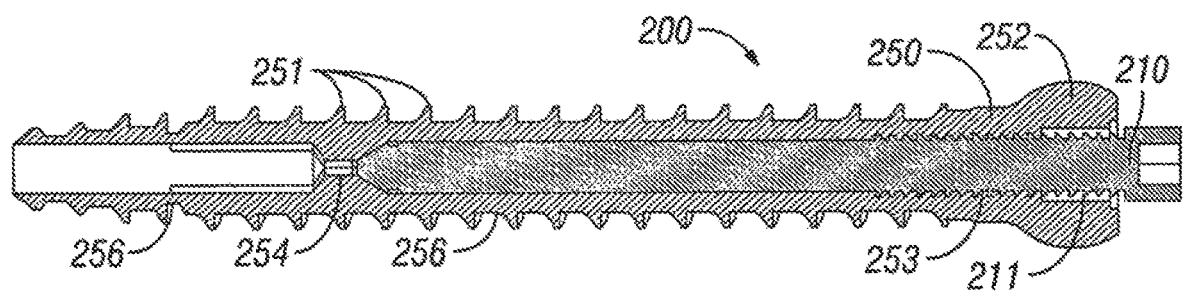
FIG. 5 shows a cutaway view of an expanding screw according to an additional aspect of the disclosure.

FIG. 5 shows a cutaway view of an expanding screw according to an additional aspect of the disclosure. The bone screw 200 may have two components: a central shaft 210 with standard male threads 211 and an outer body 250 with bone threads 251. The outer body component 250 may also provide the screw head 252 and standard female threads 253. The screw head 252 may interface with the tulip assembly (not shown), provide a driver portion for interfacing with a driver (not shown), or both. Mating threads 211, 253 located on the central shaft 210 and the outer body 250 may allow for relative translation between the two. While a driver (not shown) holds the outer body 250 in position, the shaft 210 may be threaded down into the outer body 250. The shaft 210 may, in turn, contact a reduced, stepped, or narrowed inner diameter 254 of the outer body 250. This contact may cause a dimensional interference between the central shaft 210 and the outer body 250. The screw 250 diameter may expand by an amount equal to the dimensional interference between the shaft 210 and outer body 250 as the center shaft 210 "forces" the outer body 250 to expand radially. Axial cuts 255 and circumferential cuts 256 in the outer body 250 may allow for expansion to occur in the distal region. These axial and circumferential cuts 255, 256 may be aligned with the smaller inner diameter 254 of the outer body 250.

Figure 6A:
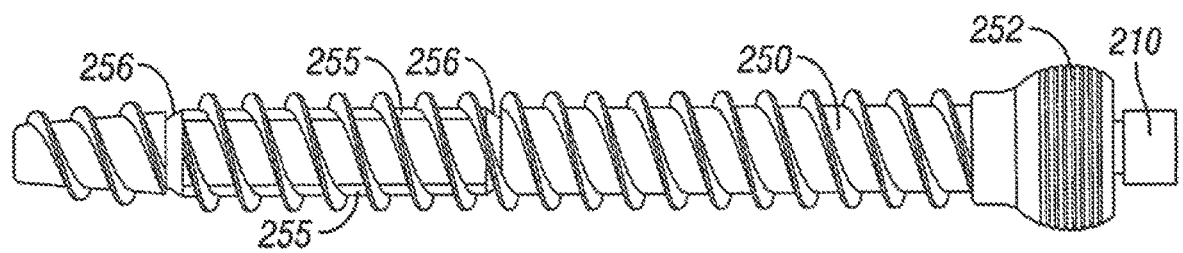
FIG. 6A shows the expanding screw of FIG. 5 without expansion.
Figure 6B:
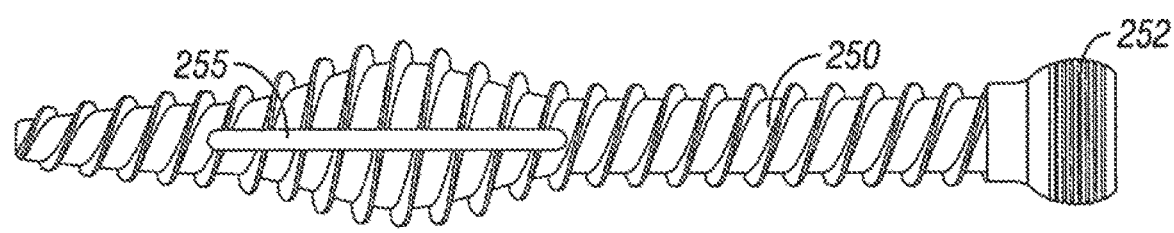
FIG. 6B shows the expanding screw of FIG. 5 with expansion in the distal region.

FIG. 6A shows the expanding screw of FIG. 5 without expansion, and FIG. 6B shows the expanding screw of FIG. 5 with expansion in the distal region. A bone screw 200, constructed according to the current aspect, may permit full expansion of the screw along the distal one-third of the screw, which may compress cancellous bone in the vertebral body and reduce or prevent fracture of the pedicle. In addition, bone screw 200 may be fully collapsible, which may permit full revision without disrupting the pedicle path any more so than is done during insertion of the screw. Bone screw 200 may expand enough to significantly increase the pullout force, and it may expand so as to prevent or reduce toggling or migration when subjected to in vivo biomechanical forces. Finally, the expansion of bone screw 200 may increase the purchase of the screw in the bone without negatively affecting the initial purchase, i.e. before actuation.

As noted above, the interface between pedicle screws and the vertebrae is critical for the stability of posterior spinal fusion constructs. As patients age, osteoporosis and other factors decrease the potential stability of the bone-screw interface, particularly in the cancellous region of the vertebral body. In general, as the surface area in which the screw contacts the bone is increased, so is the strength or the construct.

A further aspect of the disclosure provides a way to locally increase the surface contact area of the bone-screw interface in the region of greatest need, inside the cancellous vertebral body. This may be achieved by mechanically increasing the diameter of the screw in the distal one-third of the screw after the screw has been inserted into the vertebral body in a collapsed position.

Screws constructed according to this aspect of the invention may increase the distal diameter of the screw via mechanical actuation. Furthermore, such screws may have a poly-axial design and include components that are compatible with other poly-axial designs and systems, such as, e.g., a tulip, a clamp, a wedge, and a bone screw with threads.

Figure 7:
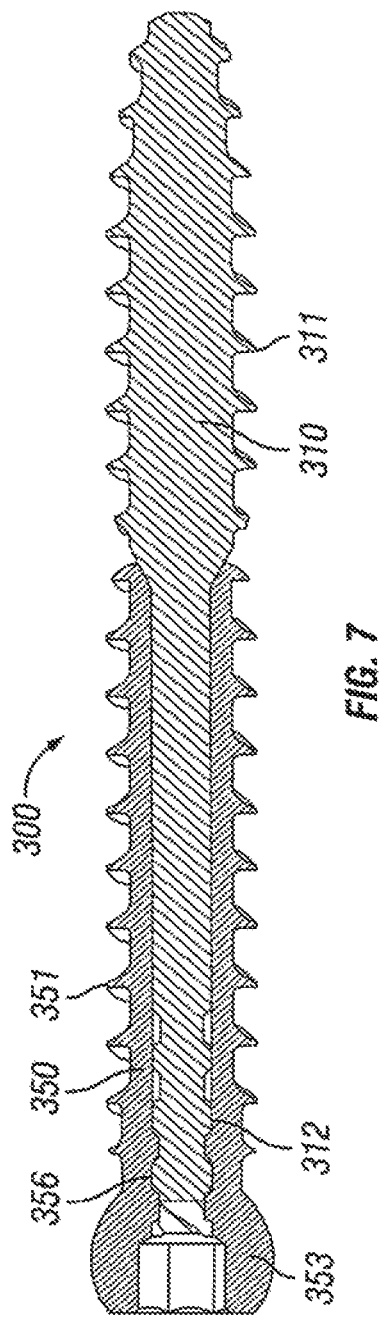
FIG. 7 shows a cutaway view of an expanding screw, without any expansion, according to a further aspect of the disclosure.
Figure 8:
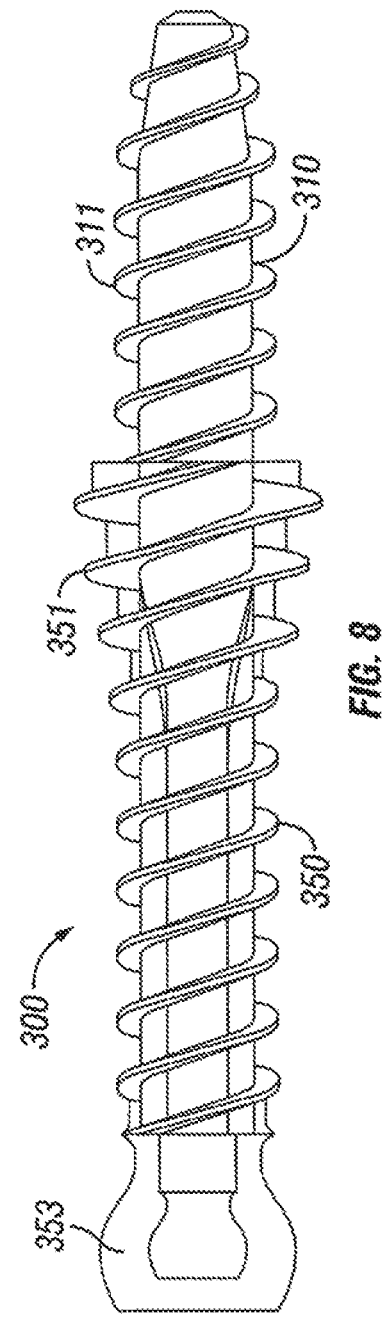
FIG. 8 shows the expanding screw of FIG. 7 with expansion in the distal region.

FIG. 7 shows a cutaway view of an expanding screw, without any expansion, according to a further aspect of the disclosure, and FIG. 8 shows the expanding screw of FIG. 7 with expansion in the distal region. The bone screw 300 may include two components 310, 350. Each component may have bone threads 311, 351, as well as specifically designed mating threads 312, 352 (male and female, respectively) having the same pitch and lead as the bone threads 311, 351. Component 310 may provide distal bone threads 311 and a smaller diameter shaft that carries the male portion 312 of the mating threads. Component 350 may provide the proximal bone threads 351 and screw head 353. The screw head 353 may interface with the tulip assembly (not shown), provide a driver portion for interfacing with a driver (not shown), or both. Component 350 may also contain a through-hole that provides the female portion 352 of the mating threads.

In use, component 350 may be threaded onto component 310 to as shown in FIG. 7. Then, the assembly 300 may be inserted into the vertebral body by a means of dual driver design (not shown) that prevents either component from moving relative to the other. Once fully inserted, component 310 may be held in place by a driver, while component 350 may be threaded farther down the shaft of component 310 as shown in FIG. 8. The inner diameter of the through-hole in component 350 may contact the threads (larger diameter) of component 310. As a result, the diameter of component 350 may be forced outward. This increase in diameter may be aided by cuts running parallel to the screw axis (not shown).

The inner threads 352 may have the same pitch and lead as the "outer" bone threads 311. When component 350 is threaded down, the bone threads 311 on the outside of component 310 may not be wiped away as the diameter increases. The threads 352 in the expanding region of component 350 may cut into the bone, creating enhanced fixation within the vertebral body.

Bone screw 300, constructed according to the current aspect, may permit full expansion of the screw along the distal one-third of the screw, which may compress cancellous bone in the vertebral body and reduce or prevent fracture of the pedicle. In addition, bone screw 300 may be fully collapsible, which may permit full revision without disrupting the pedicle path any more so than is done during insertion of the screw. Bone screw 300 may expand enough to significantly increase the pullout force, and it may expand so as to prevent or reduce toggling or migration when subjected to in vivo biomechanical forces. Finally, the expansion of bone screw 300 may increase the purchase of the screw in the bone without negatively affecting the initial purchase, i.e. before actuation.

Although each of the above-noted aspects have been described for a specific use in vertebrae, the aspects may also be used in other types of bone. Additionally, each of the aspects may include constructions for use with medical tools for insertion and removal. In this regard, the aspect may include surfaces or drive portions for this purpose.

While the disclosure has been described in terms of exemplary embodiments, those skilled in the art will recognize that the disclosure can be practiced with modifications in the spirit and scope of the appended claims. These examples given above are merely illustrative and are not meant to be an exhaustive list of all possible designs, embodiments, applications or modifications of the disclosure.

What is claimed is:

1. A method of stabilizing a spine comprising the steps of:
providing a bone screw comprising:
a first component comprising a proximal shaft and a distal portion, the proximal shaft comprising male mating threads, the distal portion comprising bone threads;
a second component extending from a proximal end to a distal end and comprising an outer surface and an inner through-hole, the outer surface comprising bone threads, the inner through-hole comprising female mating threads configured to mate with the male mating threads of the proximal shaft, the second component having a first position with the distal end without any expansion and the second component having a second position with the distal end expanded when the female mating threads are threaded over the bone threads of the distal portion of the first component, and
wherein the proximal shaft has a smaller diameter than the distal portion of the first component,
positioning the bone screw within a vertebral body of the spine.

2. The method of claim 1, wherein the bone threads of the first component are more distal than the mating threads along the first component.

3. The method of claim 1, wherein the female mating threads of the second component have the same pitch as at least some of the male mating threads and bone threads of the first component.

4. The method of claim 1, wherein the second component includes a rounded screw head with a driver portion for interfacing with a driver.

5. The method of claim 1, wherein the first component has a greater length than the second component.

6. The method of claim 1, wherein the female mating threads of the second component have the same pitch and lead as the bone threads of the first component.

7. The method of claim 1, wherein a distal one-third of the second component expands when the second component is fully threaded onto the first component.

8. The method of claim 1, wherein the bone screw consists essentially of polyether ether ketone (PEEK).

9. A method for stabilizing a spine comprising steps of:
providing a bone screw comprising:
a first component comprising a proximal shaft and a distal portion extending from the proximal shaft, the first component comprising a first set of threads and a second set of threads; and
a second component extending from a proximal end to a distal end and comprising an outer surface and an inner through-hole, the inner through-hole comprising mating threads configured to mate with the first set of threads on the first component, the second component having a first position with the distal end without any expansion and the second component having a second position with the distal end expanded when the inner through-hole contacts the second set of threads of the first component, and
wherein the proximal shaft has a smaller diameter than the distal portion of the first component,
positioning the bone screw in a vertebral body.

10. The method of claim 9, wherein the second set of threads is more distal than the first set of threads along the first component.

11. The method of claim 9, wherein the mating threads of the second component have the same pitch as at least some of the first set of threads and the second set of threads of the first component.

12. The method of claim 9, wherein the second component includes external bone engaging threads.

13. The method of claim 9, wherein the second component includes a rounded screw head having a driver portion for interfacing with a driver.

14. The method of claim 9, wherein the first component has a greater length than the second component.

15. The method of claim 9, wherein the second set of threads of the first component is configured to engage bone.

16. A method of stabilizing a spine comprising the steps of:
providing a bone screw comprising:
a first component comprising a proximal shaft and a distal portion, the first component comprising a first set of threads along a portion of the proximal shaft and a second set of threads along a portion of the distal portion; and
a second component extending from a proximal end to a distal end and comprising an outer surface and an inner through-hole, the outer surface comprising bone threads, the inner through-hole comprising mating threads configured to mate with the first set of threads on the first component, the second component having a first position with the distal end without any expansion and the second component having a second position with the distal end expanded when the inner through-hole contacts the distal portion of the first component, and
wherein the proximal shaft has a smaller diameter than the distal portion of the first component,
positioning the bone screw in a vertebral body.

17. The method of claim 16, wherein in the second position, the distal end of the second component has an increased diameter relative to the first position, and the proximal end remains a constant diameter relative to the first position.

18. The method of claim 16, wherein in the second position, the bone threads of the second component are expanded.

* * * * *